United States Patent [19]
Roberts

[11] Patent Number: 5,403,285
[45] Date of Patent: Apr. 4, 1995

[54] APPARATUS FOR SECURING A CATHETER TUBE TO A BODY

[76] Inventor: Sandra L. Roberts, 1206 Fairway Dr., Salina, Kans. 67401

[21] Appl. No.: 235,359

[22] Filed: Apr. 29, 1994

[51] Int. Cl.6 ............................................. A61M 25/02
[52] U.S. Cl. ..................................................... 604/179
[58] Field of Search ........................ 604/179, 174, 180

[56] References Cited

U.S. PATENT DOCUMENTS

| | | | |
|---|---|---|---|
| 4,582,508 | 4/1986 | Pavelka | 604/179 |
| 4,666,432 | 5/1987 | McNeish et al. | 604/174 |
| 5,048,512 | 9/1991 | Turner et al. | 604/179 X |

OTHER PUBLICATIONS 7-page brochure entitled Caremark Homecare–Changing The Central Catheter Dressing (1988) by Caremark Homecare Inc., an affiliate of Baxter Healthcare Corporation.

*Primary Examiner*—John D. Yasko
*Attorney, Agent, or Firm*—Henderson & Sturm

[57] ABSTRACT

An apparatus for holding a catheter of a type having a flexible tube which can have one end thereof which extends into a large vein near a heart. The tube has a closure cap on the other end thereof for allowing the introduction of medications or fluids into the blood in the tube so that they can be quickly mixed with blood and thereby transported to other parts of the body for permitting blood to be quickly withdrawn therefrom. An elongated, flexible, elastic member is adapted to extend completely around the chest of a person and over the flexible tube at the location where the tube exits the body. Hook and loop closure members are provided on the flexible members for holding the tube in a coiled position adjacent the flexible member. The flap is provided with hook and loop fasteners for selectively covering up the coiled tube when not in use, but allowing easy access to the tube for adding medications, drawing blood, or to change the entire securing apparatus from time to time so that it can be washed, cleaned and re-used. Also, elastic and has hook and loop fasteners on the ends thereof so that it can be easily stretched and fastened around the chest.

5 Claims, 2 Drawing Sheets

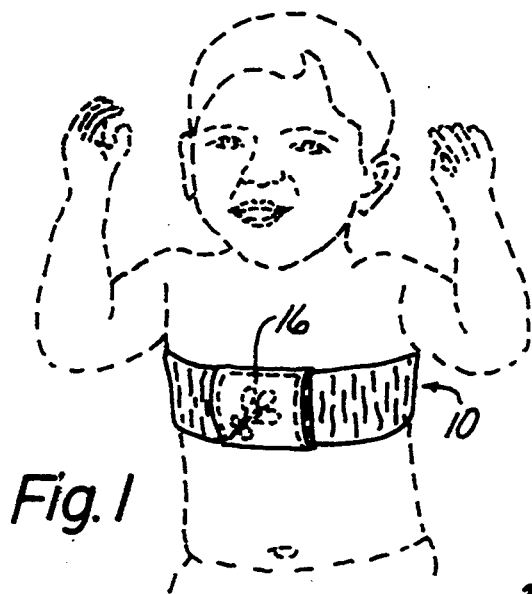
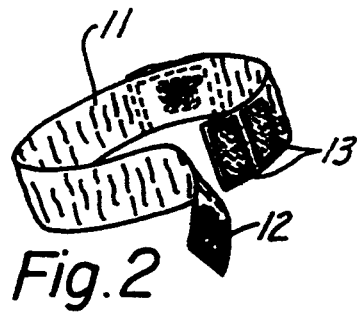
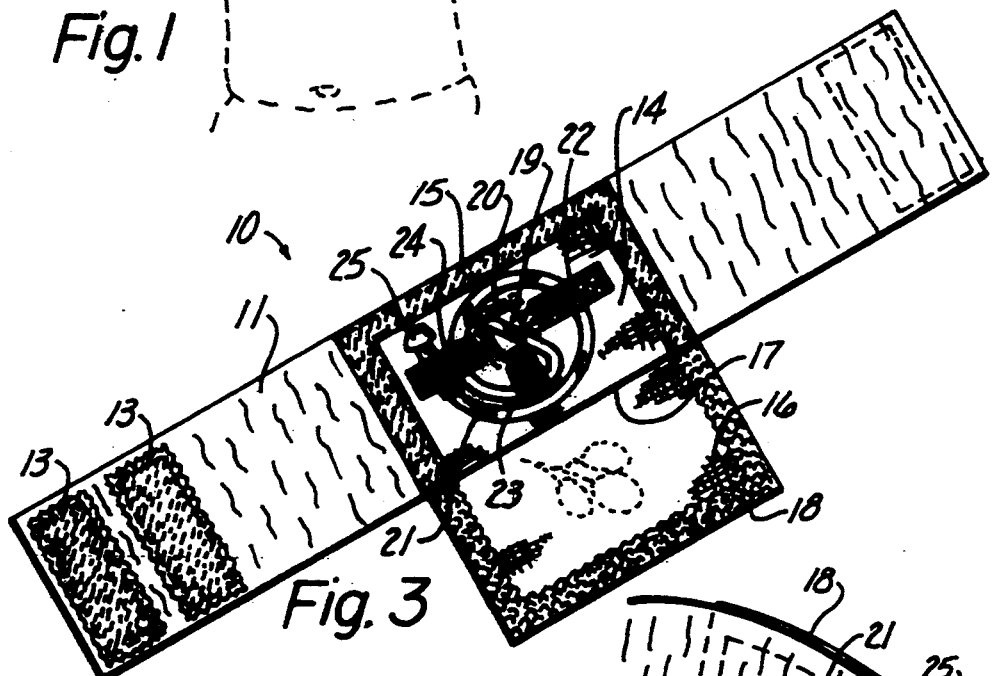
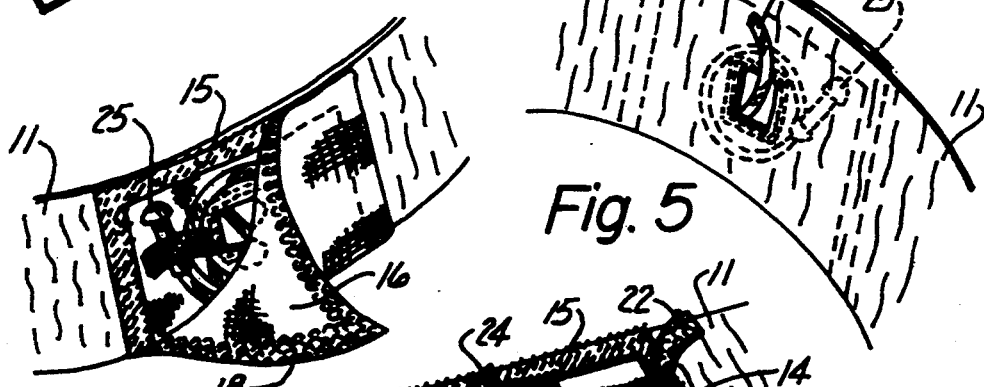
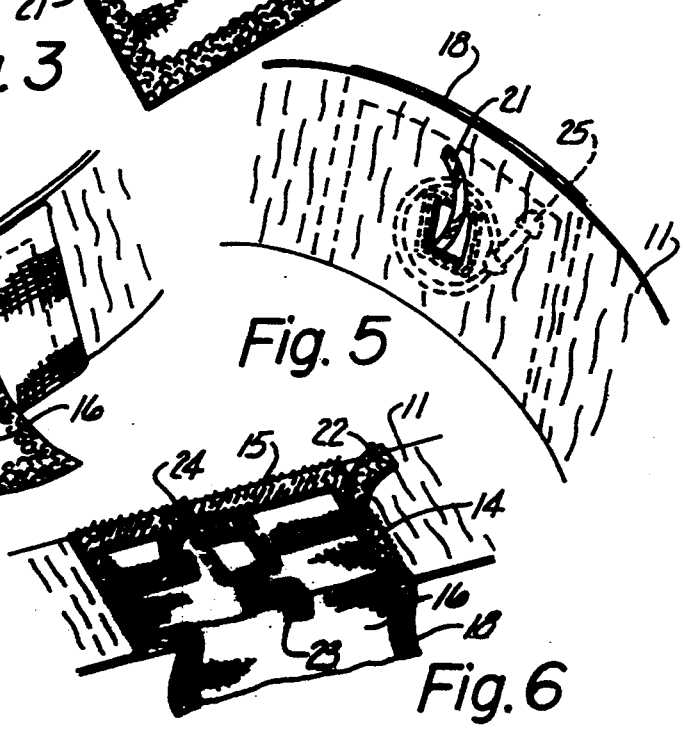

5,403,285

APPARATUS FOR SECURING A CATHETER TUBE TO A BODY

TECHNICAL FIELD

The present invention relates generally to an apparatus for holding a catheter tube to a body, and more particularly to such a device which eliminates the need for applying and removing tape to a body which can cause soreness and discomfort.

BACKGROUND ART

A central catheter is sometimes used by implanting it in a person or in an animal, sometimes for long periods of time. This catheter can be, for example, a flexible silicone tube having a tip which is placed in a large vein near the heart, so that medications for fluids can be mixed quickly with the blood and transported to other parts of the body. The catheter is then brought under the skin along the chest wall and leaves the body at another place on the chest or stomach, sometimes referred to as the "exit site." The external part of the catheter is several inches long and has a cap covering the end. Around the middle of the catheter there is typically a dacron cuff. The dacron cuff serves two purposes. As the body heals, tissues will go around the cuff to hold the catheter in place and it also prevents germs from traveling up the outside of the catheter.

Many procedures have been developed at preventing infection and one of these procedures involves taping a dressing or gauze pad over the exit site and securing it with tape. This dressing must be changed on a regular basis and the area thereunder cleaned and disinfected. Because this process is necessary quite frequently, the process of securing tape to a body and removing it at frequent intervals causes a redness or soreness. Because of the discomfort associated with this process, there is a need for an apparatus and process to eliminate the taping and tape removal procedures.

DISCLOSURE OF THE INVENTION

The present invention relates generally to an apparatus for holding a catheter of a type having a flexible tube which can have one end thereof which extends into a large vein near a heart. The tube has a closure cap on the other end thereof for allowing the introduction of medications or fluids into the blood in the tube so that they can be quickly mixed with blood and thereby transported to other parts of the body and for permitting blood to be quickly withdrawn therefrom.

An elongated, flexible, elastic member is adapted to extend completely around the chest of a person or the body and chest of an animal, and over the flexible tube at the location where the tube exits the body. Hook and loop closure members are provided on the flexible members for holding the tube in a coiled position adjacent the flexible member. The flap is provided with hook and loop fasteners for selectively covering up the coiled tube when not in use, but allowing easy access to the tube for adding medications, drawing blood, or to change the entire securing apparatus from time to time so that it can be washed, cleaned and re-used. Also the flexible elastic member has hook and loop fasteners on the ends thereof so that it can be easily stretched and fastened around the chest.

An object of the present invention is to provide an apparatus to secure and hold the part of a catheter which extends from the body to eliminate the old process of taping a gauze bandage around the place where the catheter exists the body, thereby eliminating the need to secure and remove tape when changing the gauze bandage which otherwise causes soreness to the body.

Another object of the present invention is to provide a comfortable holder for the portion of the catheter which extends outside of the body.

A further object of the present invention is to provide an apparatus which can be easily cleaned and re-used.

Other objects, advantages, and novel features of the present invention will become apparent from the following detailed description of the invention when considered in conjunction with the accompanying drawings.

BRIEF DESCRIPTION OF THE DRAWINGS

FIG. 1 shows a preferred embodiment of the present invention attached around the chest of a baby which is shown in dashed lines in FIG. 1;

FIG. 2 is a perspective view of the preferred embodiment of FIG. 1 from behind and showing the catheter extending through an opening in the flexible member and showing the hook and loop fastener on the ends of the flexible member;

FIG. 3 is a top plan view of the preferred embodiment with the flap open and hook and loop fasteners holding the catheter tube and tip in a coiled position;

FIG. 4 is a perspective view showing the front flap pulled away partially from its hook and loop fastener to show how the catheter can be stored to keep it clean and out of sight;

FIG. 5 is an enlarged partial perspective view showing how the catheter extends through an opening in the elastic, flexible strap and shows in dashed lines where the catheter tube and the cap thereof is located;

FIG. 6 is an enlarged perspective view of the central portion of the preferred embodiment of FIGS. 1-5 and showing hook and loop fasteners which are useful to open and close to hold the coiled tube of the catheter;

BEST MODES FOR CARRYING OUT THE INVENTION

Figure 7:
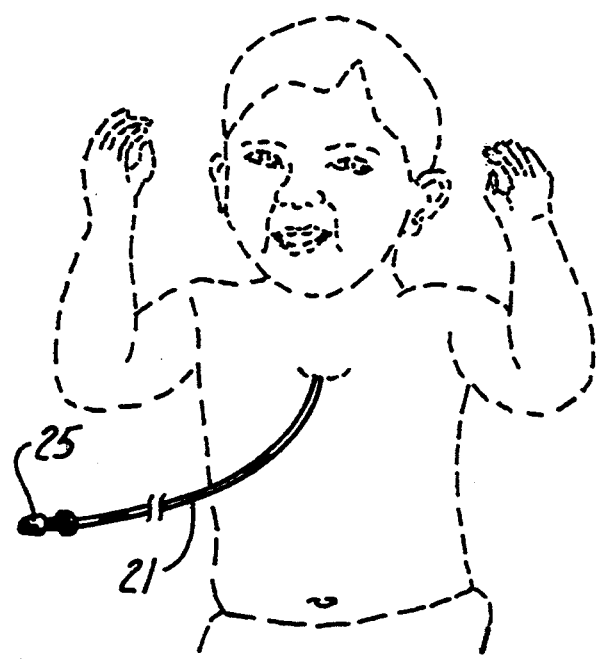
FIG. 7 shows how the catheter extends out of the center of a child's chest.

Referring now to the drawings wherein like reference numerals designate identical or corresponding parts throughout the several views, FIG. 1 shows an apparatus (10) attached around the chest of a baby which has a catheter installed into its body and exiting from the center of its chest as shown in FIG. 7. A flexible material (11) also has elastic in it and is preferably of a type used to stretch and wrap ankles or other body parts which have been sprained. This material is similar to the material commonly referred to as Spandex, which is easily stretched to a point at which it becomes tight. The flexible member (11) has hooks (12) on one end thereof and loops (13) on the other end thereof so that when the members (12) and (13) are pressed together, they will hold as in the Velcro brand hook and loop fasteners.

A cotton cloth (14) is sewn to the flexible member (11) and has loops (15) around three sides. Cotton flap

(16) is sewn to the flexible member (11) and can be a continuous cotton piece with the cotton piece (14) if desired. This flap (16) folds along line (17) so that the hook fasteners (18) which extend around three sides of the flap (16) can engage the loop fastener (15).

An opening (19) is disposed through the flexible member (11) and through the cotton cloth member (14) and threads (20) are shown where the cotton cloth (14) is sewn around the hole (19) to the flexible member (11). The catheter tube (21) extends through the opening (19) and is held in place by hook and loop fasteners (22), (23) and (24). A cap (25) is provided which allows needles to extend therethrough for inserting liquid medications, or to withdraw blood. This cap (25) is of a self-healing substance such as latex rubber so that when the needle is withdrawn it will remain sealed.

To use the apparatus (10) shown in FIGS. 1-6, the catheter tube (21) would be threaded through the opening (19) as shown in FIG. 3 with the hook and loop fasteners (22), (23) and (24) in the open position shown in FIG. 6. A person would grasp the ends of the flexible material (11) and stretch it as it is wrapped around the baby shown in FIG. 1. The hook and loop fasteners (12) and (13) are then attached and the elasticity of the material (11), because it is stretched, will apply a constant tightening pressure against the chest of the baby. This can be adjusted so that it is comfortable while at the same time serving to hold the device securely in place. Once the flexible material (11) is secured around the infant, the tube (21) is coiled, for example, to the position shown in FIG. 3 and the hook and loop fasteners (22), (23) and (24) are pushed together to hold the catheter tube (21) and tip (25) in place, for example, in the position shown in FIGS. 3 and 4. Then the flap closure (16) is moved from the position shown in FIG. 3 to the position shown in FIG. 4 and ultimately to the position shown in FIG. 1. This will hold the catheter tube (21) and tip (25) in place, it will keep the tube and tip clean and out of sight until it is needed. When it is desired to add fluids such as medication, chemotherapy or the like, the flap (16) can be pulled open and the liquids or medication inserted through the tip (25) as is necessary. Blood can also be drawn out through the tip (25) if desired. Of course when this procedure is complete, the flap (16) can be closed again to the FIG. 1 position.

Figure 8:
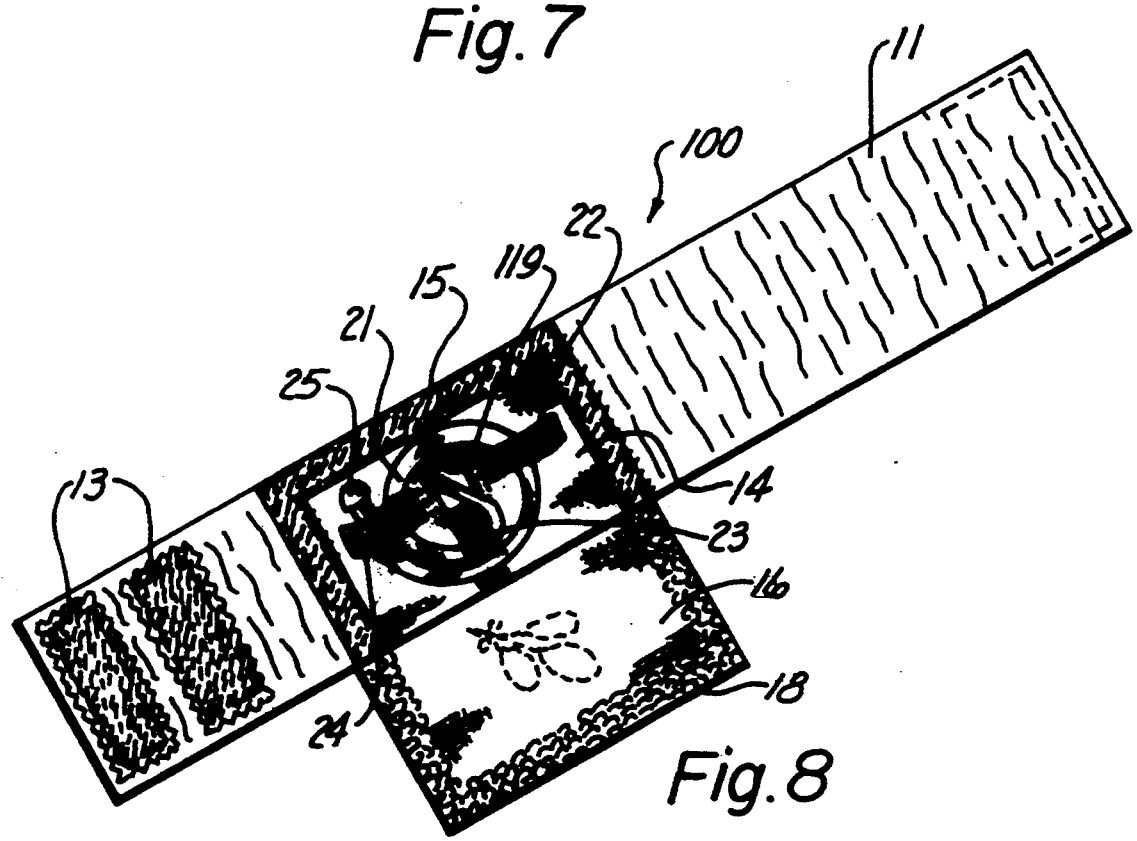
FIG. 8 shows an alternate embodiment of the present invention adapted more for the use of an adult than the FIG. 1-6 embodiment, which is designed more for use by children.

FIG. 8 shows an adult embodiment (100) which is like the embodiment of FIGS. 1-6 in all respects except for the placement of the hole (119) and the placement of member (14) and flap (16). The reason for the placement of the adult version being different is so that the person wearing the catheter (21) can install and remove the apparatus (100) by him or herself, because the hook and loop closures would then be in the front of the person, instead of at the rear of the person as in the embodiment (10) designed for infants.

Obviously, many modifications and variations of the present invention are possible in light of the above teachings. It is therefore to be understood that, within the scope of the appended claims, the invention may be practiced otherwise than as specifically described.

I claim:

1. Apparatus for holding a catheter of a type having a flexible tube which can have one end thereof which extends into a large vein near a heart, said tube having a closure cap on the other end thereof for allowing the introduction of medications or fluids into the blood in the tube so that they can be quickly mixed with the blood and thereby transported to other parts of a body or permitting blood to be quickly withdrawn therefrom, said apparatus comprising:

an elongated flexible member adapted to extend completely around said body and over the flexible tube at the location where said tube exits said body; and further provided with releasably closure means on opposite ends of said elongated flexible member wherein said flexible member also includes a generally centrally disposed opening dimensioned to receive said flexible tube;

enclosure means associated with said member for completely enveloping said tube and having an enclosure opening wherein said enclosure means is provided with a first fastening means for securing the periphery of said enclosure opening; and, a second fastening means disposed within said enclosure means for captively engaging a portion of said tube.

2. The apparatus of claim 1 wherein said first fastening means comprises hook and loop type closures connected to said flexible member for selectively enveloping said tube relative to said flexible member.

3. The apparatus of claim 2 wherein said second fastening means comprises at least one hook and loop type fastener.

4. The apparatus of claim 1 wherein said flexible member is also elastic.

5. The apparatus of claim 2 wherein said second fastening means includes a plurality of spaced apart hook and loop type fasteners for captively engaging selected portions of said flexible tube.

* * * * *